US008617196B2

(12) United States Patent
Binmoeller

(10) Patent No.: US 8,617,196 B2
(45) Date of Patent: Dec. 31, 2013

(54) METHOD AND APPARATUS FOR PERFORMING NEEDLE GUIDED INTERVENTIONS

(71) Applicant: Xlumena, Inc., Mountain View, CA (US)

(72) Inventor: Kenneth F. Binmoeller, Rancho Santa Fe, CA (US)

(73) Assignee: Xlumena, Inc., Mountain View, CA (US)

( * ) Notice: Subject to any disclaimer, the term of this patent is extended or adjusted under 35 U.S.C. 154(b) by 0 days.

(21) Appl. No.: 13/709,960

(22) Filed: Dec. 10, 2012

(65) Prior Publication Data

US 2013/0226218 A1  Aug. 29, 2013

Related U.S. Application Data

(62) Division of application No. 11/886,499, filed as application No. PCT/US2005/044158 on Dec. 7, 2005, now Pat. No. 8,328,837.

(60) Provisional application No. 60/634,254, filed on Dec. 8, 2004.

(51) Int. Cl.
*A61B 17/34* (2006.01)

(52) U.S. Cl.
USPC ...................................... 606/185; 604/164.01

(58) Field of Classification Search
USPC ........... 606/185; 604/101.04, 164.01, 167.01, 604/167.02, 167.03, 167.04, 167.05, 604/167.06, 533, 536
See application file for complete search history.

(56) References Cited

U.S. PATENT DOCUMENTS

| 2,127,903 | A | 8/1938 | Bowen |
| 3,039,468 | A | 6/1962 | Price |
| 3,717,151 | A | 2/1973 | Collett |
| 3,874,388 | A | 4/1975 | King et al. |
| 3,970,090 | A | 7/1976 | Loiacono |
| 4,173,392 | A | 11/1979 | Ekinaka et al. |
| 4,235,238 | A | 11/1980 | Ogiu et al. |
| 4,587,972 | A | 5/1986 | Morantte, Jr. |
| 4,608,965 | A | 9/1986 | Anspach, Jr. et al. |
| 4,705,040 | A | 11/1987 | Mueller et al. |
| 4,790,813 | A | 12/1988 | Kensey |
| 4,869,263 | A | 9/1989 | Segal et al. |
| 4,896,678 | A | 1/1990 | Ogawa |

(Continued)

FOREIGN PATENT DOCUMENTS

| EP | 637431 A1 | 2/1995 |
| EP | 1314404 A2 | 5/2003 |

(Continued)

OTHER PUBLICATIONS

Maisin et al.; Patency of endoscopic cystoduodenostomy maintained by a Z stent; Gastrointestinal Endoscopy; 40(6); pp. 765-768; Nov. 1994.

(Continued)

*Primary Examiner* — Ryan Severson
*Assistant Examiner* — Jonathan W Miles
(74) *Attorney, Agent, or Firm* — Shay Glenn LLP

(57) ABSTRACT

An apparatus and method for performing needle guided interventions and especially needle guided dilations of tissue to create a therapeutic conduit between two luminal organs or structures. The device is particularly useful for creation of an artificial lumen between two hollow body organs using the working lumen of an endoscope.

4 Claims, 7 Drawing Sheets

(56) References Cited

U.S. PATENT DOCUMENTS

| | | |
|---|---|---|
| 4,917,097 A | 4/1990 | Proudian et al. |
| 4,920,967 A | 5/1990 | Cottonaro et al. |
| 4,950,285 A | 8/1990 | Wilk |
| 4,973,317 A | 11/1990 | Bobrove |
| 4,990,139 A | 2/1991 | Jang |
| 5,024,655 A | 6/1991 | Freeman et al. |
| 5,064,435 A | 11/1991 | Porter |
| 5,180,392 A | 1/1993 | Skeie et al. |
| 5,183,464 A | 2/1993 | Dubrul |
| 5,197,971 A | 3/1993 | Bonutti |
| 5,207,229 A | 5/1993 | Winters |
| 5,209,727 A | 5/1993 | Radisch, Jr. et al. |
| 5,211,651 A | 5/1993 | Reger et al. |
| 5,221,258 A | 6/1993 | Shturman |
| 5,224,945 A | 7/1993 | Pannek, Jr. |
| 5,226,421 A | 7/1993 | Frisbie et al. |
| 5,234,447 A | 8/1993 | Kaster et al. |
| 5,246,007 A | 9/1993 | Frisbie et al. |
| 5,257,990 A | 11/1993 | Nash |
| 5,258,000 A | 11/1993 | Gianturco |
| 5,261,920 A | 11/1993 | Main et al. |
| 5,275,610 A | 1/1994 | Eberbach |
| 5,275,611 A | 1/1994 | Behl |
| 5,290,249 A | 3/1994 | Foster et al. |
| 5,304,198 A | 4/1994 | Samson |
| 5,330,497 A | 7/1994 | Freitas et al. |
| 5,353,785 A | 10/1994 | Wilk |
| 5,372,588 A | 12/1994 | Farley et al. |
| 5,395,349 A | 3/1995 | Quiachon et al. |
| 5,443,484 A | 8/1995 | Kirsch et al. |
| 5,458,131 A | 10/1995 | Wilk |
| 5,462,561 A | 10/1995 | Voda |
| 5,470,337 A | 11/1995 | Moss |
| 5,495,851 A | 3/1996 | Dill et al. |
| 5,520,700 A | 5/1996 | Beyar et al. |
| 5,536,248 A | 7/1996 | Weaver et al. |
| 5,588,432 A | 12/1996 | Crowley |
| 5,601,588 A | 2/1997 | Tonomura et al. |
| 5,603,698 A | 2/1997 | Roberts et al. |
| 5,620,456 A | 4/1997 | Sauer et al. |
| 5,620,457 A | 4/1997 | Pinchasik et al. |
| 5,662,664 A | 9/1997 | Gordon et al. |
| 5,688,247 A | 11/1997 | Haindl et al. |
| 5,697,944 A | 12/1997 | Lary |
| 5,709,671 A | 1/1998 | Stephens et al. |
| 5,709,707 A | 1/1998 | Lock et al. |
| 5,713,870 A | 2/1998 | Yoon |
| 5,725,552 A | 3/1998 | Kotula et al. |
| 5,797,906 A | 8/1998 | Rhum et al. |
| 5,817,062 A | 10/1998 | Flom et al. |
| 5,827,276 A | 10/1998 | LeVeen et al. |
| 5,843,116 A | 12/1998 | Crocker et al. |
| 5,843,127 A | 12/1998 | Li |
| 5,853,421 A | 12/1998 | Leschinsky et al. |
| 5,855,576 A | 1/1999 | LeVeen et al. |
| 5,857,999 A | 1/1999 | Quick et al. |
| 5,858,006 A | 1/1999 | Van der Aa et al. |
| 5,882,340 A | 3/1999 | Yoon |
| 5,893,856 A | 4/1999 | Jacob et al. |
| 5,897,567 A | 4/1999 | Ressemann et al. |
| 5,935,107 A | 8/1999 | Taylor et al. |
| 5,944,738 A | 8/1999 | Amplatz et al. |
| 5,951,576 A | 9/1999 | Wakabayashi |
| 5,951,588 A | 9/1999 | Moenning |
| 5,957,363 A | 9/1999 | Heck |
| 5,993,447 A | 11/1999 | Blewett et al. |
| 6,007,522 A | 12/1999 | Agro et al. |
| 6,007,544 A | 12/1999 | Kim |
| 6,017,352 A | 1/2000 | Nash et al. |
| 6,022,359 A | 2/2000 | Frantzen |
| 6,036,698 A | 3/2000 | Fawzi et al. |
| 6,074,416 A | 6/2000 | Berg et al. |
| 6,080,174 A | 6/2000 | Dubrul et al. |
| 6,113,609 A | 9/2000 | Adams |
| 6,113,611 A | 9/2000 | Allen et al. |
| 6,190,353 B1 | 2/2001 | Makower |
| 6,228,039 B1 | 5/2001 | Binmoeller |
| 6,231,515 B1 | 5/2001 | Moore et al. |
| 6,231,587 B1 | 5/2001 | Makower |
| 6,241,758 B1 | 6/2001 | Cox |
| 6,251,084 B1 | 6/2001 | Coelho |
| 6,290,485 B1 | 9/2001 | Wang |
| 6,309,415 B1 | 10/2001 | Pulnev et al. |
| 6,322,495 B1 | 11/2001 | Snow et al. |
| 6,334,446 B1 | 1/2002 | Beyar |
| 6,348,064 B1 | 2/2002 | Kanner |
| 6,358,264 B2 | 3/2002 | Banko |
| 6,371,964 B1 | 4/2002 | Vargas et al. |
| 6,371,965 B2 | 4/2002 | Gifford et al. |
| 6,391,036 B1 | 5/2002 | Berg et al. |
| 6,402,770 B1 | 6/2002 | Jessen |
| 6,436,119 B1 | 8/2002 | Erb et al. |
| 6,447,524 B1 | 9/2002 | Knodel et al. |
| 6,454,765 B1 | 9/2002 | LeVeen et al. |
| 6,475,168 B1 | 11/2002 | Pugsley, Jr. et al. |
| 6,475,185 B1 | 11/2002 | Rauker et al. |
| 6,475,222 B1 | 11/2002 | Berg et al. |
| 6,485,496 B1 | 11/2002 | Suyker et al. |
| 6,488,653 B1 | 12/2002 | Lombardo |
| 6,508,252 B1 | 1/2003 | Berg et al. |
| 6,520,908 B1 | 2/2003 | Ikeda et al. |
| 6,535,764 B2 | 3/2003 | Imran et al. |
| 6,575,967 B1 | 6/2003 | Leveen et al. |
| 6,610,100 B2 | 8/2003 | Phelps et al. |
| 6,614,595 B2 | 9/2003 | Igarashi |
| 6,616,675 B1 | 9/2003 | Evard et al. |
| 6,620,122 B2 | 9/2003 | Stinson et al. |
| 6,626,919 B1 | 9/2003 | Swanstrom |
| 6,632,197 B2 | 10/2003 | Lyon |
| 6,635,068 B1 | 10/2003 | Dubrul et al. |
| 6,638,213 B2 | 10/2003 | Ogura et al. |
| 6,645,205 B2 | 11/2003 | Ginn |
| 6,656,206 B2 | 12/2003 | Corcoran et al. |
| 6,669,708 B1 | 12/2003 | Nissenbaum et al. |
| 6,682,536 B2 | 1/2004 | Vardi et al. |
| 6,736,828 B1 | 5/2004 | Adams et al. |
| 6,746,472 B2 | 6/2004 | Frazier et al. |
| 6,746,489 B2 | 6/2004 | Dua et al. |
| 6,749,621 B2 | 6/2004 | Pantages et al. |
| 6,773,440 B2 | 8/2004 | Gannoe et al. |
| 6,835,189 B2 | 12/2004 | Musbach et al. |
| 6,902,535 B2 | 6/2005 | Eberhart et al. |
| 6,916,332 B2 | 7/2005 | Adams |
| 6,921,361 B2 | 7/2005 | Suzuki et al. |
| 6,921,387 B2 | 7/2005 | Camrud |
| 6,942,678 B2 | 9/2005 | Bonnette et al. |
| 6,960,233 B1 | 11/2005 | Berg et al. |
| 6,966,917 B1 | 11/2005 | Suyker et al. |
| 6,974,467 B1 | 12/2005 | Gonzales, Jr. |
| 6,979,290 B2 | 12/2005 | Mourlas et al. |
| 7,018,401 B1 | 3/2006 | Hyodoh et al. |
| 7,056,325 B1 | 6/2006 | Makower et al. |
| 7,077,850 B2 | 7/2006 | Kortenbach |
| 7,131,948 B2 | 11/2006 | Yock |
| 7,150,723 B2 | 12/2006 | Meguro et al. |
| 7,153,314 B2 | 12/2006 | Laufer et al. |
| 7,156,857 B2 | 1/2007 | Pasricha et al. |
| 7,169,161 B2 | 1/2007 | Bonnette et al. |
| 7,182,771 B1 | 2/2007 | Houser et al. |
| 7,204,842 B2 | 4/2007 | Geitz |
| 7,273,451 B2 | 9/2007 | Sekine et al. |
| 7,303,531 B2 | 12/2007 | Lee et al. |
| 7,309,341 B2 | 12/2007 | Ortiz et al. |
| 7,361,180 B2 | 4/2008 | Saadat et al. |
| 7,377,897 B1 | 5/2008 | Kunkel et al. |
| 7,390,323 B2 | 6/2008 | Jang |
| 7,416,554 B2 | 8/2008 | Lam et al. |
| 7,429,264 B2 | 9/2008 | Melkent et al. |
| 7,534,247 B2 | 5/2009 | Ortiz |
| 7,591,828 B2 | 9/2009 | Ortiz |
| 7,731,693 B2 | 6/2010 | Melsheimer |
| 7,758,565 B2 | 7/2010 | Melsheimer |
| 7,845,536 B2 | 12/2010 | Viola et al. |
| 7,942,890 B2 | 5/2011 | D'Agostino et al. |

(56) References Cited

U.S. PATENT DOCUMENTS

| | | |
|---|---|---|
| 7,998,155 B2 | 8/2011 | Manzo |
| 8,034,063 B2 | 10/2011 | Binmoeller |
| 8,187,289 B2 | 5/2012 | Tacchino et al. |
| 8,328,837 B2 | 12/2012 | Binmoeller |
| 8,357,193 B2 | 1/2013 | Phan et al. |
| 8,425,539 B2 | 4/2013 | Binmoeller et al. |
| 2001/0011170 A1 | 8/2001 | Davison et al. |
| 2002/0183787 A1 | 12/2002 | Wahr et al. |
| 2002/0188301 A1 | 12/2002 | Dallara et al. |
| 2003/0014063 A1 | 1/2003 | Houser et al. |
| 2003/0032975 A1 | 2/2003 | Bonutti |
| 2003/0040803 A1 | 2/2003 | Rioux et al. |
| 2003/0045893 A1 | 3/2003 | Ginn |
| 2003/0050665 A1 | 3/2003 | Ginn |
| 2003/0069533 A1 | 4/2003 | Kakutani et al. |
| 2003/0073979 A1 | 4/2003 | Naimark et al. |
| 2003/0078604 A1 | 4/2003 | Walshe |
| 2003/0088256 A1 | 5/2003 | Conston et al. |
| 2003/0093118 A1 | 5/2003 | Ho et al. |
| 2003/0109900 A1 | 6/2003 | Martinek |
| 2003/0120292 A1 | 6/2003 | Park et al. |
| 2003/0163017 A1 | 8/2003 | Tam et al. |
| 2003/0236536 A1 | 12/2003 | Grigoryants et al. |
| 2004/0019322 A1 | 1/2004 | Hoffmann |
| 2004/0034371 A1 | 2/2004 | Lehman et al. |
| 2004/0049157 A1 | 3/2004 | Plishka et al. |
| 2004/0073108 A1 | 4/2004 | Saeed et al. |
| 2004/0199087 A1 | 10/2004 | Swain et al. |
| 2004/0236346 A1 | 11/2004 | Parker |
| 2004/0243122 A1 | 12/2004 | Auth et al. |
| 2004/0249985 A1 | 12/2004 | Mori et al. |
| 2004/0260332 A1 | 12/2004 | Dubrul et al. |
| 2005/0033327 A1 | 2/2005 | Gainor et al. |
| 2005/0043781 A1 | 2/2005 | Foley |
| 2005/0059890 A1 | 3/2005 | Deal et al. |
| 2005/0059990 A1 | 3/2005 | Ayala et al. |
| 2005/0075654 A1 | 4/2005 | Kelleher |
| 2005/0096685 A1 | 5/2005 | Murphy et al. |
| 2005/0113868 A1 | 5/2005 | Devellian et al. |
| 2005/0187567 A1 | 8/2005 | Baker et al. |
| 2005/0228413 A1 | 10/2005 | Binmoeller et al. |
| 2005/0251159 A1 | 11/2005 | Ewers et al. |
| 2005/0251208 A1 | 11/2005 | Elmer et al. |
| 2005/0277981 A1 | 12/2005 | Maahs et al. |
| 2006/0015006 A1 | 1/2006 | Laurence et al. |
| 2006/0062996 A1 | 3/2006 | Chien et al. |
| 2006/0111672 A1 | 5/2006 | Seward |
| 2006/0116697 A1 | 6/2006 | Carter et al. |
| 2006/0142703 A1 | 6/2006 | Carter et al. |
| 2006/0142790 A1 | 6/2006 | Gertner |
| 2006/0167482 A1 | 7/2006 | Swain et al. |
| 2006/0190021 A1 | 8/2006 | Hausman et al. |
| 2006/0200177 A1 | 9/2006 | Manzo |
| 2006/0217748 A1 | 9/2006 | Ortiz |
| 2006/0217762 A1 | 9/2006 | Maahs et al. |
| 2006/0224183 A1 | 10/2006 | Freudenthal |
| 2006/0259051 A1 | 11/2006 | Nissl |
| 2006/0259074 A1 | 11/2006 | Kelleher et al. |
| 2006/0282087 A1 | 12/2006 | Binmoeller |
| 2007/0027534 A1 | 2/2007 | Bergheim et al. |
| 2007/0066863 A1 | 3/2007 | Rafiee et al. |
| 2007/0112363 A1 | 5/2007 | Adams |
| 2007/0112383 A1 | 5/2007 | Conlon et al. |
| 2007/0123840 A1 | 5/2007 | Cox |
| 2007/0123917 A1 | 5/2007 | Ortiz et al. |
| 2007/0123934 A1 | 5/2007 | Whisenant et al. |
| 2007/0135825 A1 | 6/2007 | Binmoeller |
| 2007/0179426 A1 | 8/2007 | Selden |
| 2007/0197862 A1 | 8/2007 | Deviere et al. |
| 2007/0213812 A1 | 9/2007 | Webler et al. |
| 2008/0071301 A1 | 3/2008 | Matsuura et al. |
| 2008/0161645 A1 | 7/2008 | Goldwasser et al. |
| 2008/0167524 A1 | 7/2008 | Goldwasser et al. |
| 2009/0177288 A1 | 7/2009 | Wallsten |
| 2009/0227835 A1 | 9/2009 | Terliuc |
| 2009/0281379 A1 | 11/2009 | Binmoeller et al. |
| 2009/0281557 A1 | 11/2009 | Sander et al. |
| 2010/0130993 A1 | 5/2010 | Paz et al. |
| 2010/0268029 A1 | 10/2010 | Phan et al. |
| 2010/0268175 A1 | 10/2010 | Lunsford et al. |
| 2011/0137394 A1 | 6/2011 | Lunsford et al. |
| 2012/0109277 A1 | 5/2012 | Lepulu et al. |
| 2012/0130417 A1 | 5/2012 | Lepulu et al. |
| 2012/0136426 A1 | 5/2012 | Phan et al. |

FOREIGN PATENT DOCUMENTS

| | | |
|---|---|---|
| EP | 1520526 A1 | 4/2005 |
| EP | 1520532 A2 | 4/2005 |
| JP | S58-35219 | 3/1983 |
| JP | 62-233168 | 10/1987 |
| JP | H05-137794 A | 6/1993 |
| JP | H05-192407 A | 8/1993 |
| JP | H05-329165 | 12/1993 |
| JP | H05-508563 | 12/1993 |
| JP | H07-096038 | 4/1995 |
| JP | 08-071158 A | 3/1996 |
| JP | 8-504940 | 5/1996 |
| JP | 8-509639 | 10/1996 |
| JP | H08-299455 A | 11/1996 |
| JP | H09-500047 A | 1/1997 |
| JP | H09-504186 A | 4/1997 |
| JP | 10-94543 | 4/1998 |
| JP | 10-155799 A | 6/1998 |
| JP | H11-512318 A | 10/1999 |
| JP | 2000-500045 A | 1/2000 |
| JP | 2000-237303 A | 9/2000 |
| JP | 2001-511658 | 8/2001 |
| JP | 2001-275947 | 10/2001 |
| JP | 2001-517524 A | 10/2001 |
| JP | 2002-119516 | 4/2002 |
| JP | 2002-534208 A | 10/2002 |
| JP | 2003-526448 | 9/2003 |
| JP | 2004-512153 | 4/2004 |
| JP | 2004-216192 | 8/2004 |
| JP | 2005-525865 | 9/2005 |
| JP | 2007514462 | 6/2007 |
| JP | 2008-534029 A | 8/2008 |
| JP | 2009500051 | 1/2009 |
| WO | WO 97/27898 A1 | 8/1997 |
| WO | WO 00/24449 A1 | 5/2000 |
| WO | WO 01/21247 A1 | 3/2001 |
| WO | WO 01/72367 A1 | 10/2001 |
| WO | WO 03/020106 A2 | 3/2003 |
| WO | WO 03/024305 A2 | 3/2003 |
| WO | WO 03/071962 A2 | 9/2003 |
| WO | WO 2005/011463 A2 | 2/2005 |
| WO | WO 2005/096953 A1 | 10/2005 |
| WO | WO 2006/115811 A1 | 11/2006 |

OTHER PUBLICATIONS

Binmoeller et al.; U.S. Appl. No. 13/865,098 entitled "Luminal Structure Anchoring Devices and Methods," filed Apr. 17, 2013.

Brown et al.; U.S. Appl. No. 13/871,978 entitled "Methods and devices for access across adjacent tissue layers," filed Apr. 26, 2013.

Chopita et al.; Endoscopic gastroenteric anastomosis using magnets; Endoscopy; 37(4); pp. 313-317; Apr. 2005.

Fritscher-Ravens et al.; A through-the-scope device for suturing and tissue approximation under EUS control; Gastro Endo; 56(5); pp. 737-742; Nov. 2002.

Fritscher-Ravens et al.; Transgastric gastropexy and hiatal hernia repair for GERD under EUS control: A porcine model; Gastro Endo; 59(1); pp. 89-95; Jan. 2004.

Swain et al.; Knot tying at flexible endoscopy; gastro endo; 40(6); pp. 722-729; Nov. 1994.

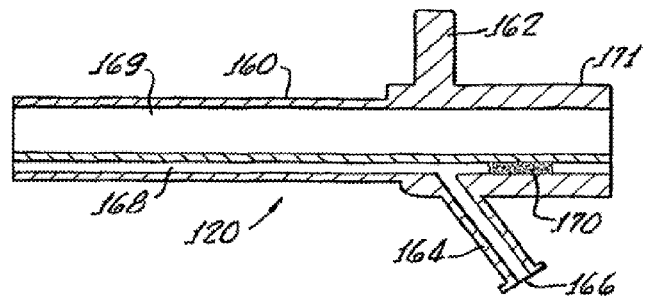
FIG. 14.
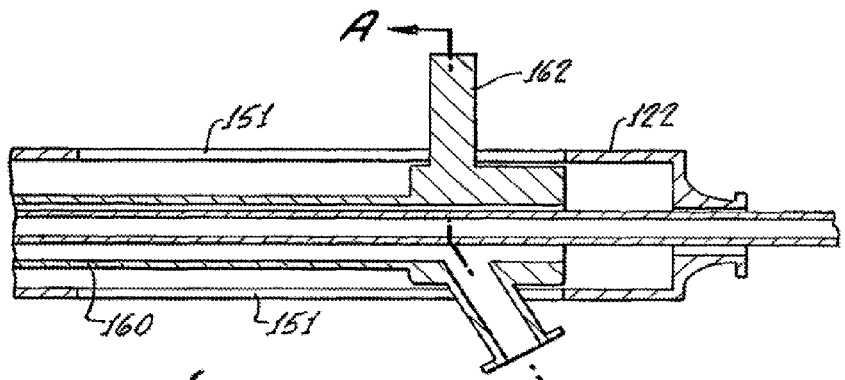
FIG. 15.
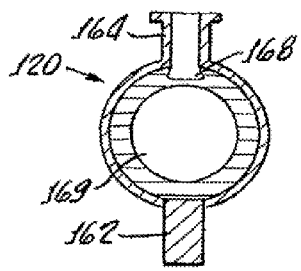 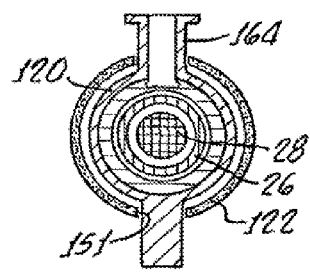 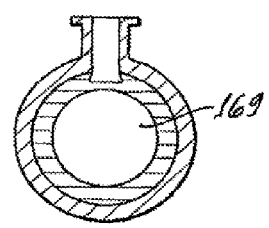
FIG. 16A.   FIG. 16B.   FIG. 16C.

METHOD AND APPARATUS FOR PERFORMING NEEDLE GUIDED INTERVENTIONS

CROSS REFERENCE TO RELATED APPLICATIONS

This application is a divisional application of U.S. patent application Ser. No. 11/886,499 filed on Sep. 14, 2007 and issued as U.S. Pat. No. 8,328,837 on Dec. 11, 2012; which is a 371 filing claiming priority to PCT Patent Application No. PCT/US2005/044158 filed on Dec. 7, 2005; which claims the benefit of priority to U.S. Provisional Application No. 60/634,254 filed on Dec. 8, 2004, the full disclosures of which are hereby expressly incorporated by reference.

BACKGROUND OF THE INVENTION

1. Field of the Invention

Disclosed is a device and method for performing needle guided interventions and especially needle guided dilations of tissue to create a therapeutic conduit between two luminal organs or structures. The device is particularly useful for creation of an artificial lumen between hollow body organs using the working lumen of an endoscope.

2. Description of the Related Art

Often there is a need to create a luminal passageway between two lumen containing organs in the body. Examples of these would be between a segment of bowel and another structure such as another section of bowel, gallbladder, bile or pancreatic duct. Often the second luminal structure is not an organ but rather a cyst, pseudocyst or abscess.

Other techniques and devices exist to perform these procedures. The creation of a conduit between a bowel lumen (stomach, colon, rectum or duodenum) and a luminal structure is performed using an ultrasound endoscope. A stylet-filled continuous stainless steel needle is advanced through the working lumen of an ultrasound endoscope and directed through the wall of the bowel and into the targeted luminal structure lying adjacent to the bowel. Once inside the structure the stylet is removed and a guidewire is advanced into the luminal structure. The needle is removed and a catheter device is advanced over the guidewire and directed through the bowel wall into the luminal structure. Examples of catheter devices are dilating bougie catheters and balloon catheters.

One example of how these procedures are typically performed is the drainage of fluid from a pseudocyst. In this procedure a stylet-filled continuous stainless steel needle is advanced through the working lumen of an endoscope and directed through the wall of the bowel and into a pseudocyst cavity lying adjacent to the bowel. Once inside the cavity, the stylet is removed and a guidewire is advanced through the needle and into the pseudocyst. The needle is removed and a balloon catheter is advanced over the guidewire and directed through the bowel wall until the deflated balloon lies across the wall of the bowel and the tissue interposed between the bowel and the pseudocyst. The balloon is then inflated creating a 6-8 mm passageway between the bowel and the pseudocyst cavity. The balloon is deflated and the catheter removed over the guidewire leaving behind an enlarged conduit. A double pigtailed drainage catheter or other drainage device is then advanced over the guidewire and one end is placed inside the pseudocyst cavity and the other inside the bowel thus facilitating the drainage of fluid from the pseudocyst into the bowel.

Another example of how these procedures are typically performed is the creation of a conduit between an obstructed bile or pancreatic duct and a bowel lumen using an ultrasound endoscope. A stylet-filled continuous stainless steel needle is advanced through the working lumen of an ultrasound endoscope and directed into the bile or pancreatic duct upstream from the site of obstruction. Once inside the duct, the stylet is removed and a guidewire is advanced through the needle and into the duct. The needle is removed and a dilating catheter or balloon catheter is advanced over the guidewire and directed into the duct. A stent is then advanced over the guidewire and one end is placed inside the duct and the other inside the bowel.

However the procedures as described above are often difficult to complete successfully because once the needle is removed, the remaining guidewire lacks the rigidity to provide adequate support for the catheter device. This makes it difficult to push the catheter device through the bowel wall and into the luminal structure. This is particularly true when the tissue interposed between the bowel lumen and the targeted luminal structure is thick, edematous or fibrotic. Often the catheter device will simply buckle inside the bowel and not advance through the wall. Furthermore, the small diameter guidewire has a tendency to dislodge during the exchange of the needle for the balloon catheter which causes a loss of lumen access and necessitates repeating the procedure. Even when successful, the physician is required to make many exchanges of the needle, guidewire and or catheters which can make the technique cumbersome and time consuming. A simpler procedure is necessary to overcome the disadvantages of current practice. Particularly, a system that will enable rapid catheter device access on the initial attempt after needle puncture of the target luminal structure and one that does not require multiple exchanges of accessories is needed. Also needed is a method of fixing the position of the needle and catheter device sheath relative to the endoscope while one or the other is advanced or retracted. Particularly, providing a more stable platform over which a catheter device sheath may be advanced is important and incorporating all the wires, sheaths and needles into a single integrated system would save the practitioner valuable time and reduce the chance of potential surgical morbidity.

BRIEF SUMMARY OF THE INVENTION

Accordingly the present invention is directed to an apparatus and method that as embodied and broadly described herein, includes a handle, a catheter device, a needle, actuators and locking members that integrate the control and movement of a catheter and a needle that are used for creation of an artificial lumen between organs, hollow bodies or two segments of bowel using the working lumen of an endoscope.

The catheter device is provided with at least one inner lumen and the needle is positioned inside the catheter device and is used to facilitate the initial puncture of the tissue and provide support so that the catheter device can be advanced over the needle and across the tissue passageway formed by the needle. The handle incorporates actuators that are attached to the catheter device and needle and are used to advance and retract the catheter device and the puncture needle along the axis of the endoscope. Locking members are provided that fix the position of the catheter device or needle relative to the endoscope.

In another aspect the present invention includes a method of forming a passageway in the wall of a hollow body organ by placing an apparatus into the working lumen of an endoscope and coupling the device to the proximal end of the endoscope. The needle is advanced by moving the actuator which is coupled to the proximal end of the needle. Once in position across the tissue wall, the needle can be fixed to the endoscope by using a locking member. The catheter device can be advanced over the needle by moving the actuator which is coupled to the proximal end of the apparatus. The catheter device can advance over the needle to cross the tissue wall. The catheter device may also contain a balloon that is useful for forming a larger passageway.

BRIEF DESCRIPTION OF THE DRAWINGS

The accompanying drawings are included to provide a further understanding of the invention and are incorporated in and constitute a part of this specification. The drawings illustrate embodiments of the invention and, together with the description, serve to explain the principles of the invention. In the drawings.

FIG. 14 is section view of the catheter actuator of FIG. 11;

FIG. 15 is a section view of the assembled catheter device and needle actuators;

FIG. 16A is a cross sectional view of the catheter actuator taken through the holder and inflation port (A-A) with the needle actuator removed;

FIG. 16B is a cross sectional view of the catheter actuator taken through the holder and inflation port (A-A) including the needle actuator and stylet;

FIG. 16C is a cross sectional view of an alternate embodiment of the catheter actuator taken through the inflation port (A-A) with the needle actuator removed;

DETAILED DESCRIPTION

Figure 1:
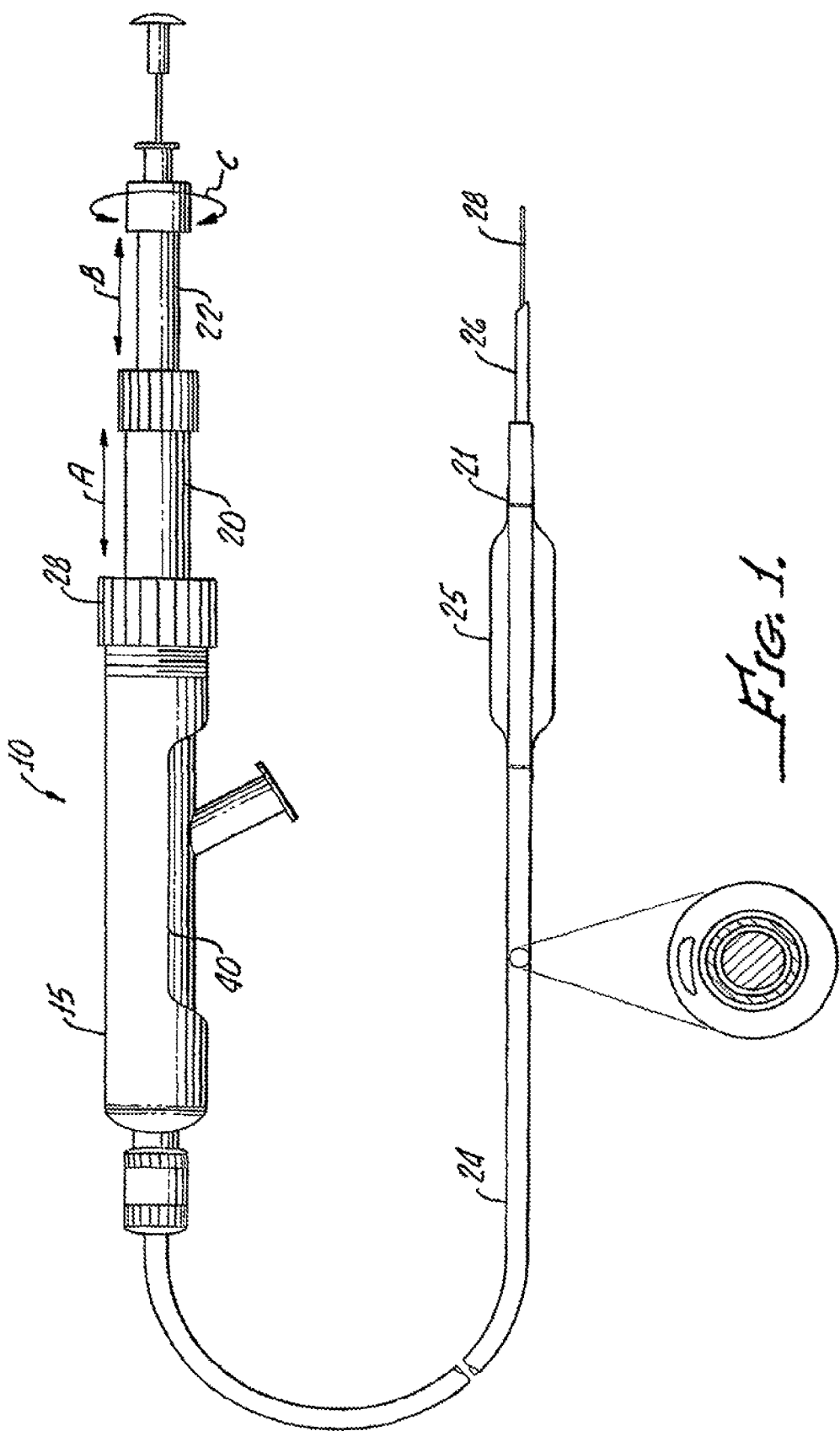
FIG. 1 is a system view of one embodiment of the apparatus.

It is to be understood that the present invention is not limited to the particular embodiments, materials, and examples described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Unless defined otherwise, all technical terms used herein have the same meanings as commonly understood by one of ordinary skill in the art to which this invention belongs. Specific methods, devices, and materials are described, although any methods and materials similar or equivalent to those described herein can be used in the practice or testing of the present invention.

Reference will now be made in detail to the present preferred embodiments of the invention, examples of which are illustrated in the accompanying drawings. Wherever possible the same reference numbers are used in the drawings and the description to refer to the same or like parts, and similar reference numerals are used to refer to similar elements.

The apparatus and method described herein may offer improvements over the techniques currently utilized to perform endoscopy or endosonography guided transluminal creation of therapeutic passageways. The apparatus performs the same result as the current medical practice described but utilizes fewer parts, requires fewer instrument exchanges and provides a more stable and solid platform for performing punctures and therapeutic interventions such as tissue dilation.

As shown in FIG. 1, the apparatus 10 utilizes a handle 15, a catheter device actuator 20 and a needle actuator 22 along with a catheter device 24 and a 22 or 23 gauge hollow sharpened needle 26. Inside the needle is a stylet 28 which fills the inner lumen of the needle in a similar manner to other over-the-wire puncture needles. As will be described, the continuous stainless steel needle is stiffer than a guidewire and provides excellent support for the coaxial advancement of catheter devices over the needle 26.

The handle 15 is designed to be held by a physician to support the apparatus 10 in one hand while the catheter device actuator 20 or the needle actuator 22 or both are manipulated. In each case described in the body of this application, it is assumed that the catheter device actuator 20 may function independently from the needle actuator 22. Although the movement of the needle actuator 22 may be described, it is anticipated that the catheter device 24 may also be simultaneously operated or sequentially operated according to the medical procedure being performed. Conversely, the needle actuator 22 and the catheter device actuator 20 may be operated together as a single unit if required. No inference as to order, sequence or dependence of the catheter device or needle movement on the other is intended.

The handle 15 is particularly useful in integrating the control of the movement of the coaxial system of catheter device 24 and needle 26 into a single location. The actuators for both the catheter device 24 and needle 26 make up a part of the handle. The operator can move the catheter device 24 and needle 26 from these actuators which can make a previously cumbersome procedure easier, less confusing and faster.

Figure 2:
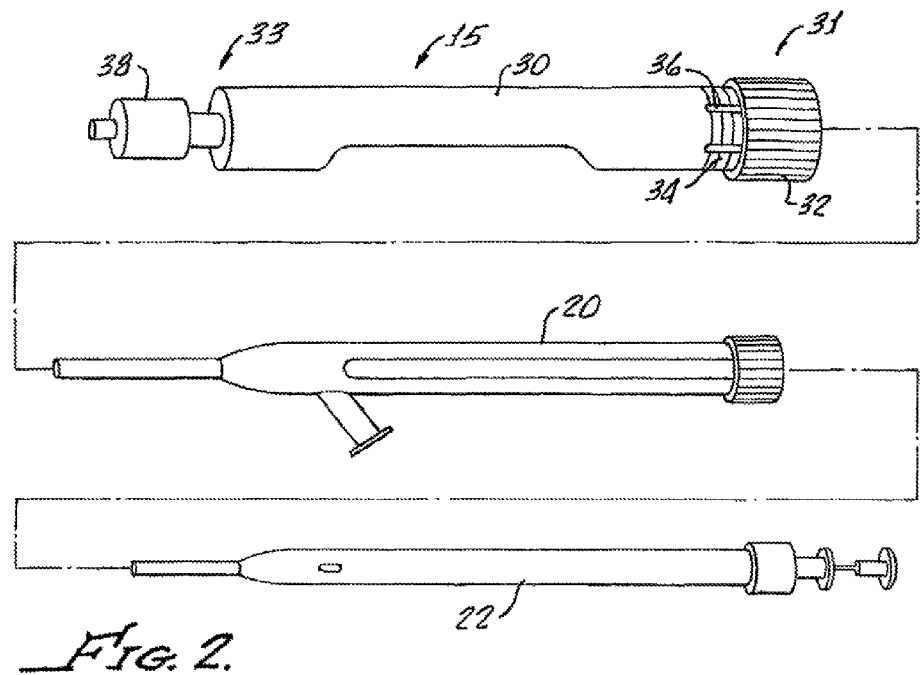
FIG. 2 is an exploded assembly view of the apparatus.

As shown in FIG. 2, the handle 15 has a body 30 that is a hollow cylindrical tube that is open at the proximal end 31. The distal end 33 is essentially closed except for a single opening that is sized for the catheter device to pass through. The body 30 functions as a housing for the catheter device and needle actuators and can be constructed from plastic or metal. The body 30 is threaded at the proximal end 31 with threads 34 designed to mate with a cap 32. The cap 32 is designed to screw onto the body 30 and partially close the proximal end 31 of the body 30. The body has one or more slits 36 running parallel to the body axis and perpendicular to the threads 34. These slits 36 intersect the threads 34 and are designed to function as a compression joint as the cap 32 is threaded onto the body. As the cap 32 is threaded onto the body, the cap 32 reduces the effective inside diameter of the body at the proximal end 31. This diameter reduction has the effect of clamping down onto the catheter device actuator 20 that is positioned inside the body and acting as a locking member.

Figure 11:
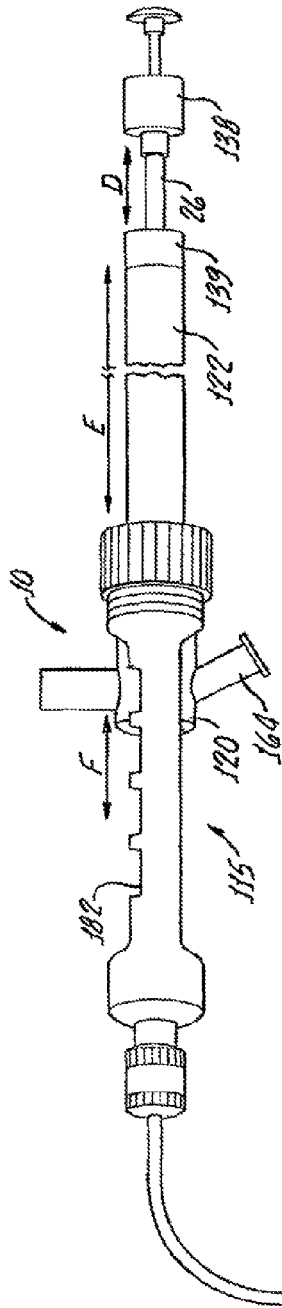
FIG. 11 is a system view of another embodiment of the apparatus.
Figure 11:
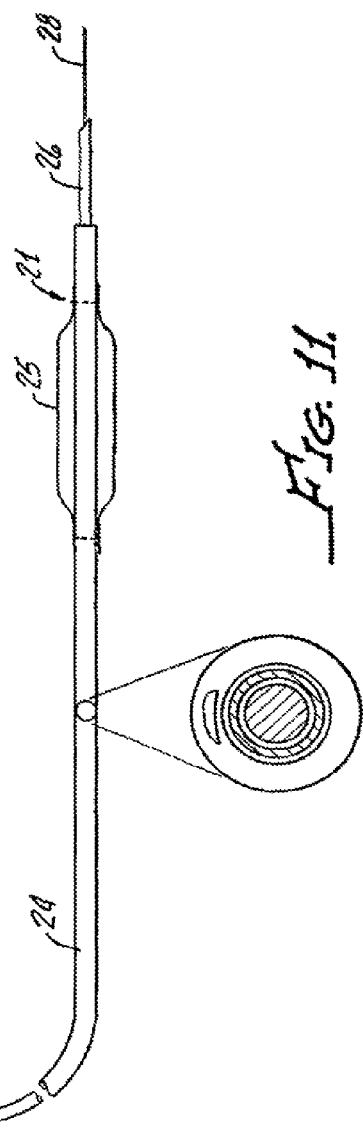

The endoscope 100 shown in FIG. 11 is an important part of the function of the apparatus 10. The apparatus 10 can function without an endoscope but the endoscope can make the performance and accordingly the success of the procedure greater. The endoscope body provides support to the catheter device as the distal portion of the catheter device is passed out of the endoscope tip. In order to push a needle across a tissue wall, often considerable force is required. The inner walls of the endoscope 100 support the catheter device 24 so that a thrust of the needle 26 is translated into a forward thrust of the needle tip 58 across a tissue wall. This is best accomplished if the catheter device 24 and the endoscope 100 are coupled. In this situation all forward movement of the catheter device 24 is expressed as a forward movement of the catheter device distal end and not a corresponding backward movement of the endoscope 100. One of the functions of the handle 15 is to join with the endoscope 100 so that any movement of the catheter device 24 or needle 26 does not cause a reverse movement of the endoscope 100 at the same time. At the distal end of the handle 33 is a connector 38 that mates with a corresponding connector on the endoscope body. The connector 38 is commonly known as a luer connector and mates to a corresponding luer connector found on the proximal end of most endoscopes.

As shown in the exploded assembly view of FIG. 2, the needle actuator 22 is sized to be placed into the inner diameter of the catheter device actuator 20. The catheter device actuator 20 is sized to be placed into the inner diameter of the body 30. The catheter device and needle actuators and the body 30 function together as a combined mechanism. As will be shown this mechanism allows for the independent movement of the catheter device 24 and the needle 26 relative to each other and the endoscope 100.

Figure 3:
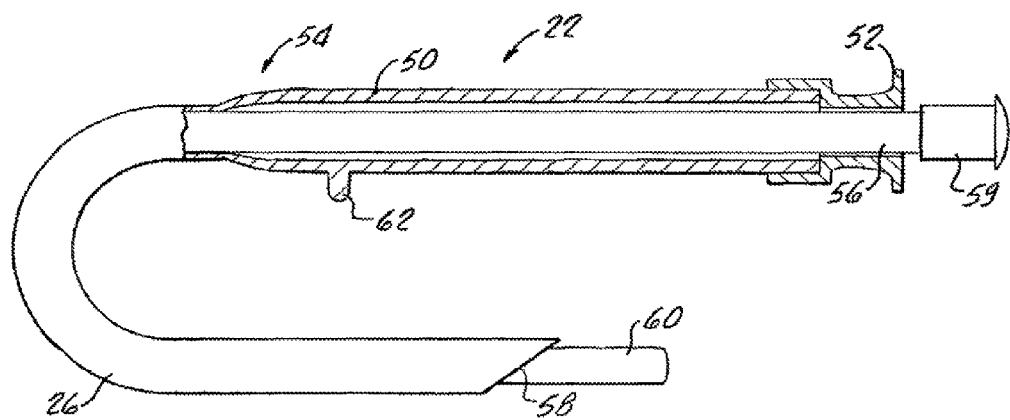
FIG. 3 is section view of the proximal end of the needle actuator showing the needle and stylet.

Turning to FIG. 3, the needle actuator 22 is shown in a section view. The needle actuator is a hollow cylindrical tube 50 with a proximal 52 and distal 54 end. The tube 50 is joined with a hollow needle 26 at the distal end 54 and has a small opening at the proximal end 52 to receive a stylet 56. The needle 26 has a sharpened end 58 that is suitable for puncturing tissue and may have an inner diameter sized to receive a stylet 56. Although a stylet 56 is shown in FIG. 3, the inclusion of a stylet 56 is not required. The stylet shown has an end plug 59 at the proximal end and a generally rounded tip 60 at the distal end. The tube 50 also has a locking tab 62 located toward the distal end 54 of its outside diameter. This locking tab 62 is used to fix the movement of the needle actuator 22 relative the endoscope 100. The tab 62 is designed to mate with a locking groove 45 located on the inner diameter of the handle body 30.

Figure 4:
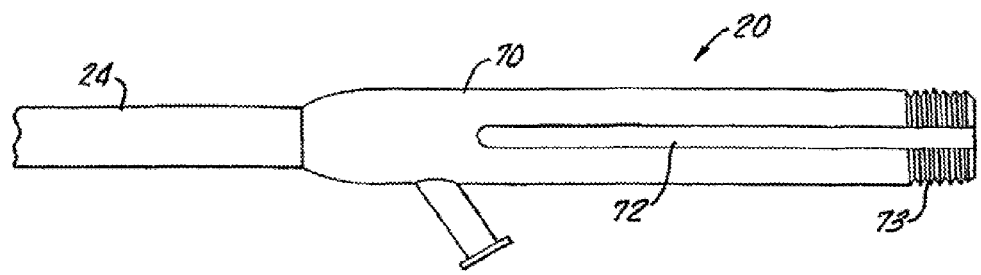
FIG. 4 is a view of the catheter device actuator.
Figure 5:
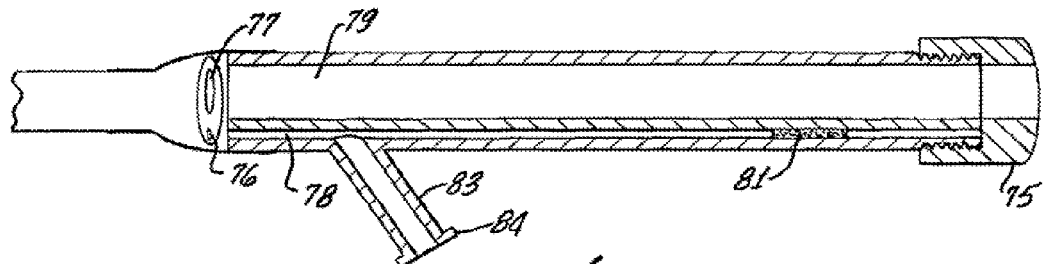
FIG. 5 is a section view of the catheter device actuator.
Figure 6:
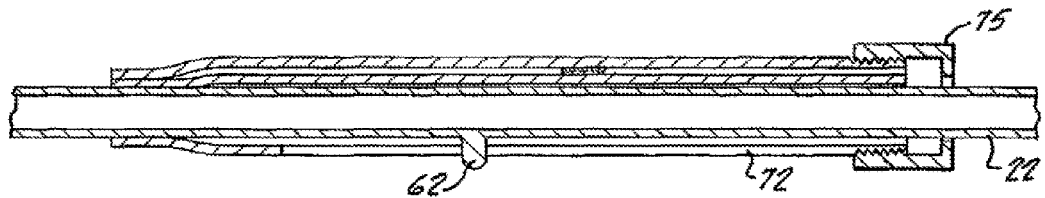
FIG. 6 is a section view of the assembled catheter device and needle actuators.

The catheter device actuator 20 is shown in greater detail in FIGS. 4-6. The catheter device actuator 20 controls the movement of the catheter device 24 and can move the catheter device 24 along the central axis of the endoscope. The catheter device actuator 20 has a housing 70 as shown in FIG. 4. The housing 70 is a hollow cylindrical tube that has a distal end and a proximal end. The distal end tapers slightly to join with the sheath 24. The body has a longitudinal slot 72 that is sized to accept the locking tab 62 of the needle body tube 50. The slot 72 is continuous from the proximal end of the housing 70 to approximately three quarters of the distance to the distal end of the housing 70. The proximal end of the body has threads 73 to accept the threads of the end cap 75. The end cap 75 prevents the needle actuator which is positioned inside the hollow interior of the housing 70 from coming out of the housing 70. However, the end cap 75 may be removed so that the needle actuator can be withdrawn from the tissue dilator if desired. The cap has a round hole at its center that allows the proximal portion 52 of the needle actuator 22 and the stylet 28 to extend outside the housing 70.

The catheter device 24 has two inner lumens that extend from the distal end to the proximal end. This catheter device 24 may be constructed from various materials such as plastic polymers, spring coils, silicone or Teflon tubing. The main lumen 77 is the larger and is designed to accept the needle body 26 and is also large enough to accommodate one 0.035" or up to two 0.021" guidewires when the needle is removed. The smaller lumen 76 is for inflating and deflating a dilation balloon attached to the distal end of the catheter device. The end of the dilation balloon 25 can be located immediately adjacent to the catheter device end 21. More preferably the distal end of the balloon can be located between the distal end of the catheter device 24 and up to 4 cm from the distal end of the catheter device. The balloon 25 has a preferred inflated diameter of between 5 and 10 mm and an effective balloon length of 3-6 cm. However various balloon lengths and diameters could be used. The catheter device may also be constructed without a dilation balloon in which case the catheter device 24 would have a single lumen and no inflation port.

The catheter device actuator 20 has two lumens corresponding to lumens of the sheath. As shown in FIG. 5, the needle lumen 79 is continuous the entire length of the housing 70. It is connected to the main lumen 77 of the sheath. The inflation lumen 78 extends from the distal end of the housing 70 and is terminated before the proximal end of the housing 70. This lumen communicates with the smaller lumen 76 of the sheath. The housing 70 has an inflation port 83 that is attached to the catheter device actuator and has a luer connector 84 at the outside end suitable for mating with an inflation syringe. The inflation port 83 is used to inflate and deflate the balloon 25. The proximal portion of the inflation lumen 78 is blocked with a plug 81 to prevent leakage of dilation fluid out the proximal end of the inflation lumen 78.

The needle actuator 22 and the catheter device actuator 20 are assembled together in FIG. 6. In this view, it can be seen how the needle actuator 22 is positioned inside the catheter device actuator 20. Also shown is the locking tab 62 which is positioned in the slot 72 and protrudes through the wall of the housing 70. Also shown is the end cap 75 which retains the needle actuator inside the hollow housing 70.

Figure 7:
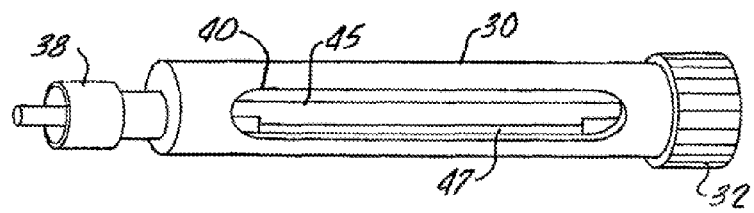
FIG. 7 is a view of the handle without the catheter device or needle actuators.
Figure 8:
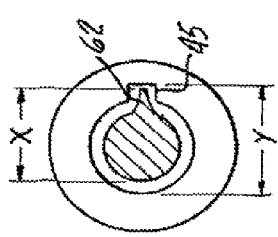
FIG. 8 is a cross sectional view of the handle body taken through the locking groove with the catheter device actuator removed.

The handle body is shown in greater detail in FIG. 7. The cylindrical body 30 has an opening 40 in the main body. This opening is located in the central portion of the body and is open to the inside of the body 30. The opening 40 is formed in the body 30 to accept the inflation port 83 of the catheter device actuator. The catheter device actuator 20 slides along the inner diameter of the body 30 and the opening provides clearance for the inflation port 83 so that the catheter device actuator 20 can be advanced, retracted and slightly rotated inside the body 30. The surface of the inside wall of the body has a locking groove 45 that is used to interface with the locking tab 62 of the needle actuator 22. The groove 45 is continuous from the proximal end of the body 30 to approximately three fourths of the distance to the distal portion of the body. The outer diameter "x" of the needle actuator tube 50 at the locking tab 62 is slightly less than the inner diameter "y" of the cylindrical body 30 measured at the groove as shown in the cross sectional view of the handle body and needle actuator in FIG. 8. In this figure the sheath actuator has been removed for clarity. The depth of the groove 45 is such that the locking tab 62 has clearance to move freely but not enough clearance to jump out of the groove 45. The locking tab 62 slides in the groove of the body 30 as the needle actuator 22 is advanced and retracted inside the catheter device activator 20.

Figure 10:
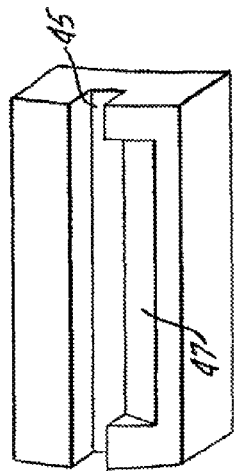
FIG. 10 is a cutaway side view of the handle body showing the locking ramp with the needle and catheter device actuators removed.
Figure 9:
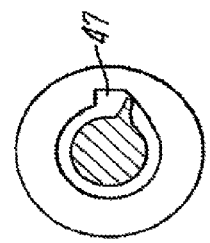
FIG. 9 is a cross sectional view of the handle body taken through the locking ramp with the catheter device actuator removed.

The groove is interrupted along its length by a locking ramp 47. The locking ramp 47, shown greater detail in FIGS. 9-10, is located along the groove 45. The depth of the locking ramp 47 varies in a radial direction. At the entrance to the locking ramp 47 at the groove 45, the depth of the locking ramp 47 is the same as the bottom of the groove 45 but the side wall gradually slopes to meet the inside diameter of the handle body 30. As the locking tab 62 is advanced and retracted along the groove 45, if the needle actuator body 22 is slightly rotated, the locking tab moves from the locking groove 45 and will travel onto the locking ramp 47. The locking ramp 47 restricts the free movement of the locking tab 62 along the longitudinal axis of the endoscope 100. If the needle actuator body 22 is slightly rotated, the locking tab 62 will travel along the tapering side wall and impinge upon the tapering side wall so that forward travel will eventually be stopped as the clearance is eliminated. At this point the locking tab 62 will remain essentially fixed with regard to the central axis of the endoscope. In this position tab 62 acts as a locking member. If the needle actuator body 22 is rotated even further, the locking tab 62 will continue to travel along the tapering side wall and will wedge itself along the side wall with a hard stop. In this way it is possible for the operator to lock the lateral movement of the needle actuator 22 relative to the endoscope 100 while still permitting movement of the catheter device actuator 20. The operator also has control as to the degree of resistance felt. A slight rotation increases frictional drag but the needle actuator body 22 can still be moved along the endoscope axis. Further rotation increases drag even further until the needle activator body 22 is fixed.

The assembled apparatus is shown in FIG. 1 shows how the various parts are assembled together. The arrows show the directions that the actuators may travel. The needle actuator 22 can be advanced or retracted along the longitudinal axis of the endoscope according to arrow B as required which transmits the same movement to the needle inside the hollow body organ. The needle actuator preferably can travel less than 10 cm. The needle actuator can more preferably travel between 4 and 8 cm. Similarly the catheter device actuator 20 can be advanced or retracted along the longitudinal axis of the endoscope according to arrow A as required which transmits the same movement to the catheter device 24 inside the hollow body organ or structure. The catheter device actuator 20 preferably can travel less than 10 cm. The catheter device actuator 20 can more preferably travel between 4 and 8 cm. The movement of either actuator can also be locked with respect to the endoscope while permitting movement of the other actuator. The needle actuator 20 is locked by rotating it according to C as required which moves the locking tab 62 along the locking ramp 47. The catheter actuator 22 is locked in position by screwing down the cap 32 located at the proximal end 31 of the handle body 30. This apparatus permits the operator to easily control the location and movement of both the needle 26 and catheter device 24. In this way the needle 26 can be advanced first, its position fixed and then the catheter device 24 can be advanced over the needle 26 without concern that the needle 26 will travel further into the tissue at the same time. This might provide for a safer and easier procedure.

An alternative embodiment of the apparatus 10 is shown in FIG. 11. In this embodiment the apparatus 10 utilizes a handle 115, a catheter actuator 120 and a needle actuator 122 along with a catheter device 24 and a 22 or 23 gauge hollow sharpened needle 26. Similarly to the previous embodiment, a stylet 28 can fill the inner lumen of the needle 26.

The handle 115 is designed to be held by a physician to support the apparatus 10 while the catheter actuator 120 or the needle actuator 122 or both are manipulated. In each case, it is assumed that the catheter device 24 and the needle 26 of this embodiment may function as a single unit or independently from each other. That is the catheter actuator 120 and the needle actuator 122 may be simultaneously or sequentially operated. The handle 115 is particularly useful in integrating the control of the movement of the coaxial system of catheter device 24 and needle 26 into a single location. The actuators for both the catheter device 24 and needle 26 make up a part of the handle 115. The operator can move the catheter device 24 and needle 26 from these actuators.

Figure 12:
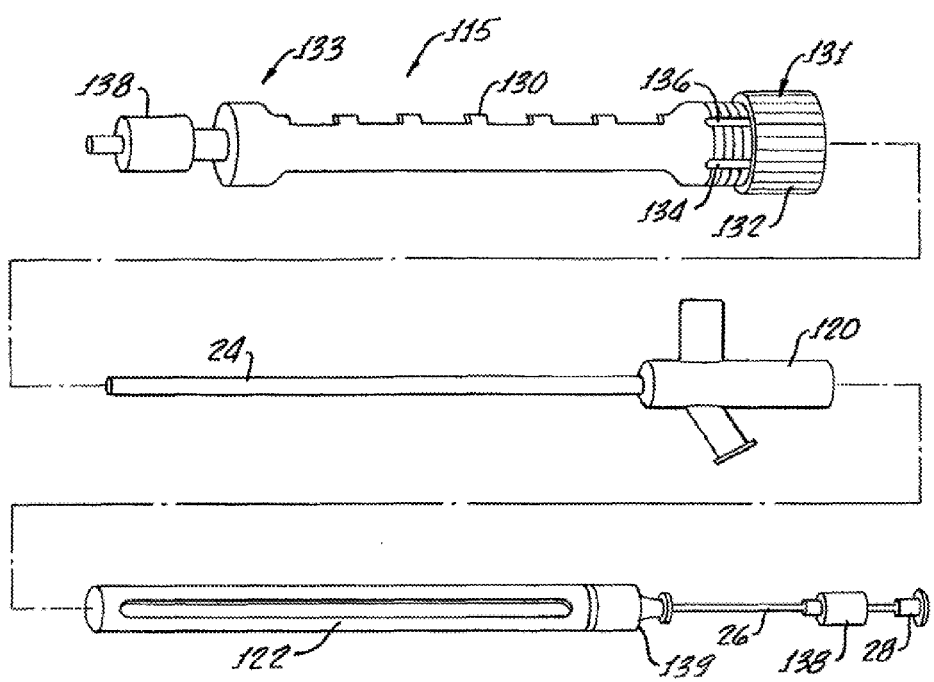
FIG. 12 is an exploded assembly view of the apparatus of FIG. 11.

As shown in FIG. 12, the handle 115 has a body 130 that is a hollow cylindrical tube that is manufactured with the proximal end 131 open. The distal end 133 is essentially closed except for a single opening that is sized for the catheter device to pass through. The body 130 functions as a housing for the catheter device and needle actuators and can be constructed from plastic, metal or other suitable material. The body 130 is threaded at the proximal end 131 with threads 134 designed to mate with a cap 132. The cap 132 is designed to screw onto the body 130 and partially close the proximal end 131 of the body 130. The body has one or more slits 136 running parallel to the body axis and perpendicular to the threads 134. These slits 136 intersect the threads 134 and are designed to function as a compression joint as the cap 132 is threaded onto the body. The cap 132 reduces the effective inside diameter of the body at the proximal end 131 to act as a locking member to clamp down onto the needle actuator 122.

The handle 115 couples with the endoscope 100 so that any movement of the catheter device 24 or needle 26 does not cause a reverse movement of the endoscope 100 at the same time. A connector 138 at the distal end of the handle 133 mates with a corresponding connector on the endoscope body. The connector 138 is preferably a luer connector but any connector that can couple the handle and endoscope together is acceptable. The needle 26 is sized to slide inside the needle actuator 122 and inside the inner diameter of the catheter device 24. The proximal end of the needle 26 has a hub 138 that is attached to the needle and the hub 138 is designed to couple with a corresponding connector 139 on the proximal end of the needle actuator 122. This hub 138 facilitates the attachment of the needle to the needle actuator 122 for movement of the needle by the actuator. The hub 138 can be disconnected from the connector 139 and the needle actuator 122 to remove the needle 26 from the needle actuator 122 and the body 130. The needle actuator 122 is sized to slide over the outside of the catheter actuator 120 and then inside the inner diameter of the body 130. The catheter and needle actuators and the body 130 function together as a combined mechanism.

Figure 13:
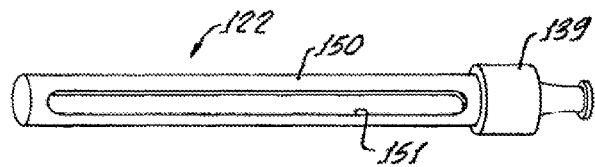
FIG. 13 is view of the needle actuator of FIG. 1.

The needle actuator 122 is shown in greater detail in FIG. 13. The needle actuator 122 is a hollow cylindrical tube 150. The distal end is open and the proximal end terminates at the connector 139. The inside diameter of the needle actuator 122 is sized to fit along the outside diameter of the catheter actuator 120. Generally the dimensions of the two diameters are close to one another so that the catheter actuator 120 can travel inside the tube 150 freely but the travel should be smooth and without unusual wobble. The tube 150 has one or more slits 151 that run longitudinally along the major length of the tube 150. The slits are continuous from the outside diameter of the tube 150 through the wall of the tube 150 to the inside diameter. If more than one slit is utilized, the slits 151 should be symmetrically arranged around the circumference of the tube 150.

The catheter actuator 120 is shown in greater detail in FIGS. 14-16. The catheter actuator 120 controls the movement of the catheter device 24 and can move the catheter device 24 along the central axis of the endoscope 100. The catheter device actuator 120 has a housing 160, a holder 162 and an inflation port 164 on the opposite side of the holder 162 as shown in FIG. 14. Similar to the previous embodiment, the catheter device 24 that is coupled to the catheter actuator 120 has two inner lumens that extend from the distal end to the proximal end. The main lumen 77 is the larger and is designed to accept the needle body 26 and is also large enough to accommodate one 0.035" or up to two 0.021" guidewires when the needle is removed. The smaller lumen 76 can be used for inflating and deflating a dilation balloon 25 attached to the distal end of the catheter device 24. The catheter device 24 may also be constructed without a dilation balloon in which case the catheter device 24 would have a single lumen and no inflation port.

The inflation lumen 168 is in fluid communication with the smaller lumen 76 of the catheter device 24 and the inflation port 164 of the catheter actuator 120. The inflation port 164 has a luer connector 166 at the outside end suitable for attaching to an inflation syringe. The inflation port 164 is used to inflate and deflate the balloon 25. The proximal portion of the lumen 168 is blocked with a plug 170 to prevent leakage of dilation fluid out the proximal end of the inflation lumen 168. The needle lumen 169 connected to the larger lumen 77 of the catheter device 24 and is open at both ends to receive the needle 26. The holder 162 is coupled to the housing 160 and is used by the operator to advance and retract the catheter actuator 120 along the handle 115. The holder 162 is long enough to extend through the needle actuator body 150 and the handle 115. Although a holder 162 and an inflation port 164 are shown, it is possible to combine the functions of these into one device. In this alternate embodiment, the inflation port 164 would serve as fluid injection site and as a holder so that the operator could use it to manipulate the catheter actuator. This embodiment would eliminate the holder 162 and would require only one slit 151 in the tube 150. This embodiment may be simpler to operate and less expensive. The proximal end 171 of the housing may be lengthened as necessary to insure that some part of the housing is always secure inside the body 115 when the catheter actuator is advanced. The housing is sized to fit snugly inside the needle actuator body 122.

The catheter actuator 120 and the needle actuator 122 are assembled together in FIG. 15. In this view, it can be seen how the needle actuator 122 is positioned outside the catheter actuator 120 but the needle 26 is positioned inside the catheter actuator 120. The holder 162 and the inflation port 164 are shown extending through the slits 151 of the needle actuator 122. FIG. 16A shows a cross section of the catheter actuator 120 taken along section A-A with the needle actuator 122 removed. FIG. 16B shows a cross section of the same catheter actuator 120 taken along section A-A with the needle actuator 122 in place. The slits 151 are shown with the holder 162 and inflation port 164 extending through these slits. The needle 26 and stylet 28 are shown in the center of lumen 169. FIG. 16C shows a cross section of the same catheter actuator 120 taken along section A-A with the needle actuator 122 and the holder 162 removed. In this embodiment the inflation port 164 functions as an inflation fluid introduction site and as a holder. In this embodiment there is only one slit 151 in the needle actuator body 150.

The cylindrical body 115 has two openings in the main body as shown in FIGS. 11 and 12. These openings are located in the central portion of the body and are typically spaced 180.degree. apart. The openings are formed in the body 115 to accept the holder 162 and inflation port 164. The catheter actuator 120 slides along the inner diameter of the body 115 and the openings provide clearance for the holder 162 and inflation port 164 so that the catheter device actuator 20 can be advanced, retracted and even slightly rotated inside the body 115. Along one edge of both openings, again positioned 180.degree. apart, are a series of locking members 182 that are used to interface with the holder 162 and the inflation port 164. As the catheter actuator is advanced, the holder 162 and inflation port 164 move in a distal direction along their respective openings in the body 115. The holder 162 and inflation port 164 can be radially rotated slightly so that the holder and inflation port move into one of these locking members 182 that are sized to accept the holder 162 and the inflation port 164. Once the holder 162 and inflation port 164 are positioned in the locking member 182, their distal movement along the body 115 is prevented. In this way the operator can advance the catheter device 24 until the tip is positioned correctly in the body and then lock the position of the catheter device 24 relative to the endoscope 100.

The assembled apparatus is shown in FIG. 11 and this figure illustrates how the various parts are assembled together. The arrows show the directions that the actuators travel. The needle 26 and stylet 28 can be moved in the directions D as shown. Once the needle 26 is coupled to the needle actuator 122 using the hub 138 and connector 139, the needle 26 and the needle actuator 122 can be moved like a single unit along the inside walls of the body 115 in the directions E. This is accomplished by grasping the connector 139 or the outside of the actuator body and moving it distally while holding the handle 115. Likewise the catheter actuator 120 can be advanced along the inside walls of the needle actuator 122 by using the holder 162 in the directions F as shown. A slight rotational movement, not shown, applied to the holder 162 or the inflation port 164 causes these to move into any one of a number of locking slots 182 located along the edge of the slots. The needle actuator 122 preferably can travel less than 10 cm. The needle actuator 122 can more preferably travel between 4 and 8 cm. The catheter device actuator 120 preferably can travel less than 10 cm. The catheter device actuator 120 can more preferably travel between 4 and 8 cm. The movement of either actuator can also be locked with respect to the endoscope. The movement of the needle actuator 122 can be fixed to the endoscope by tightening the cap 32. This causes the inside diameter of the body 115 to be reduced which impinges on the hollow cylindrical tube 150 of the needle actuator 122. The movement of the catheter actuator 120 can be fixed to the endoscope by rotating the holder 162 into one of the locking slots previously described.

Figure 17:
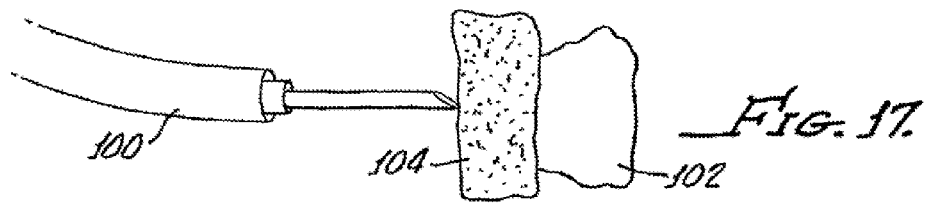
FIG. 17 is a view of the distal portion of the apparatus loaded into the working channel of an endoscope and adjacent to a tissue wall.
Figure 18:
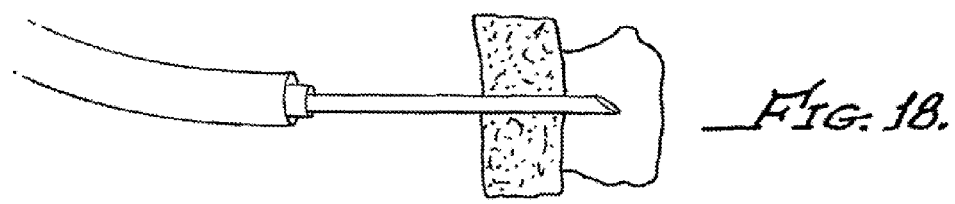
FIG. 18 is a view similar to FIG. 11 showing the needle across the tissue.
Figure 19:
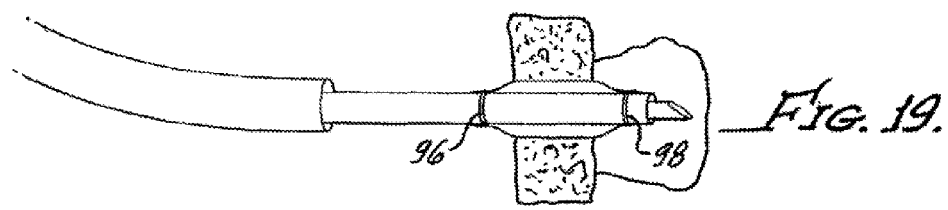
FIG. 19 is a view similar to FIG. 12 showing the catheter device across the tissue with the dilation balloon deflated.
Figure 20:
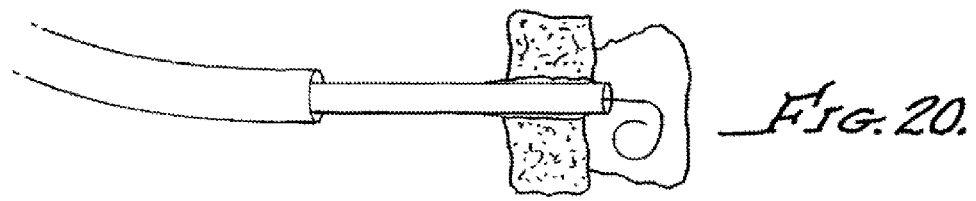
FIG. 20 is a view similar to FIG. 13 showing the needle removed and a guidewire positioned across the tissue.

As shown in FIGS. 17-21, the creation of a conduit between a bowel lumen 104 and a targeted luminal structure 102 can be performed using this system. In this procedure the stylet filled needle 26 and catheter device 24 are part of the apparatus that is introduced into the working lumen of an endoscope 100. Referring to the first embodiment, the handle 15 is secured to the outer part of the endoscope working channel using the connector 38. Once the needle 26 is positioned at the puncture site, the needle is advanced up to 8 cm and passed through the wall of the bowel and into the targeted luminal structure as shown in FIG. 20, Once inside the targeted lumen, the stylet 28 can be removed and aspiration applied or contrast medium injected under fluoroscopy to confirm entry into the target lumen. The target location shown in FIGS. 17-19 is a pseudocyst cavity 102 on the other side of the stomach wall 104 but the method may include many other target sites within the human body. The needle 26 is then locked in position by rotating the needle actuator 22 until the locking tab 62 moves into a locking ramp 47 and the needle actuator 22 is fixed. The catheter device 24 is next advanced along the stiff needle and through the tissue wall. The position of the catheter device 24 relative to the targeted lumen can be determined by visualizing the radiopaque marker(s) 96 and 97 using fluoroscopy or by injecting radiopaque dye into the proximal end of the needle with the stylet removed. In the embodiment shown, the radiopaque markers 96 and 98 are located on each end of the dilating balloon. Once at the intended position in the tissue, the catheter device 24 can be locked in position by screwing down the cap 32 of the handle body 30. If the catheter device has a dilation balloon 25 attached to its distal end, the balloon may be inflated using the inflation port 83 with either liquid or gas inflation fluid. The inflated balloon can create a passageway between the bowel and the target organ. The inflated balloon 25 also serves to anchor the sheath 24 in position so that the needle 26 can be exchanged for a guidewire. The needle 26 can be withdrawn so that one 0.035" or two 0.021" guidewires can be introduced through the catheter device 24 and into the target lumen. The balloon 25 is deflated and the catheter device 24 can be removed over the guidewire(s) leaving behind an enlarged conduit with at least one guidewire across.

Figure 21:
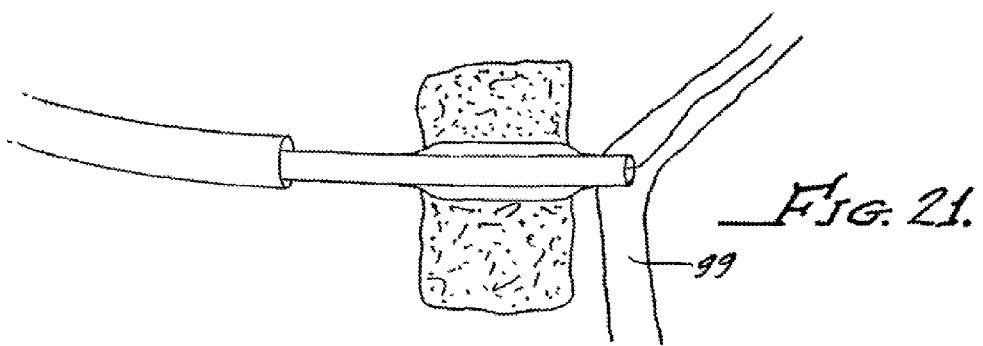
FIG. 21 is a view similar to FIG. 14 showing the catheter device with access to a duct and the guidewire positioned in the duct.

In another method, the device can function as an anchoring catheter to facilitate the placement of a guidewire into a lumen. By way of example this procedure can be used to place a guidewire into a body duct 99 as shown in FIG. 21. The duct is preferably a bile or pancreatic duct. The needle 26 is advanced under endoscopic ultrasound guidance from the duodenum or stomach through the bowel wall and into the bile or pancreatic duct using the sharpened needle tip. The catheter device 24 is then advanced over the needle 26 and into the duct 99. Once in the duct 99, the dilating balloon 25 can be optionally inflated. This may also serve as a means to provide additional anchorage to the system in the duct 99 and prevent pull-out as the needle 26 is retracted. Once the needle 26 is removed, a 0.035" guidewire can be safely placed in the duct 99 through the catheter device and once the balloon 25 is deflated the catheter device 24 can be withdrawn.

In yet another method, a pre-curved or steerable-tipped catheter can be positioned over the stylet filled needle instead of the balloon device. The curved catheter tip is useful to steer the catheter tip in different directions. By way of example this procedure can be used to place a guidewire into the bile or pancreatic ducts from an anterograde position. The needle 26 is advanced under endoscopic ultrasound guidance from the duodenum or stomach through the bowel wall and into the bile or pancreatic duct using the sharpened needle tip. A catheter is then advanced over the needle and into the duct. The needle is then exchanged for a 0.035" guidewire.

What is claimed is:

1. A method of forming a passageway in the wall of a hollow body organ comprising: placing an apparatus into the working channel of an endoscope and coupling the apparatus to the proximal end of an endoscope, positioning the distal end of the endoscope near the wall of a hollow body organ, advancing a needle across the organ wall with a needle actuator to form a passageway and fixing the needle to the endoscope using a locking member, advancing a catheter device having a distal dilation balloon over the needle and through the passageway using a catheter device actuator and fixing the catheter device to the endoscope using a locking member, and inflating the balloon to enlarge the passageway.

2. The method of claim 1 further comprising: removing the needle from inside the catheter device and placing one or more guidewires through the catheter device and into the passageway, and deflating the balloon and withdrawing the apparatus leaving the guidewire to maintain access to the passageway.

3. The method of claim 1, whereby the passageway forms a conduit between the hollow body organ and a duct.

4. The duct of claim 3, where the duct is a pancreatic duct or bile duct.

* * * * *